(12) United States Patent
Majeed et al.

(10) Patent No.: US 8,329,095 B2
(45) Date of Patent: Dec. 11, 2012

(54) PRESERVATIVE SYSTEM FOR COSMETIC FORMULATIONS—COMPOSITIONS AND METHODS THEREOF

(75) Inventors: Muhammed Majeed, Edison, NJ (US); Beena Bhat, Bangalore (IN); Garima Agarwal, Bangalore (IN)

(73) Assignee: Sami Labs Limited, Bangalore (IN)

( * ) Notice: Subject to any disclaimer, the term of this patent is extended or adjusted under 35 U.S.C. 154(b) by 0 days.

(21) Appl. No.: 13/437,194

(22) Filed: Apr. 2, 2012

(65) Prior Publication Data

US 2012/0190744 A1    Jul. 26, 2012

Related U.S. Application Data

(62) Division of application No. 12/434,747, filed on May 4, 2009, now abandoned.

(51) Int. Cl.
*A61L 2/00*    (2006.01)
*A61K 36/00*   (2006.01)

(52) U.S. Cl. ............. 422/1; 424/401; 424/405; 424/725
(58) Field of Classification Search .................. 424/725, 424/401, 405; 422/1
See application file for complete search history.

(56) References Cited

U.S. PATENT DOCUMENTS

| | | | | |
|---|---|---|---|---|
| 5,965,518 | A * | 10/1999 | Nakatsu et al. | 512/1 |
| 6,183,762 | B1 * | 2/2001 | Deckers et al. | 424/401 |
| 7,608,741 | B2 * | 10/2009 | Kim et al. | 568/730 |
| 2004/0265263 | A1 * | 12/2004 | McDonald et al. | 424/70.22 |
| 2005/0058680 | A1 * | 3/2005 | Binder et al. | 424/401 |
| 2008/0262082 | A1 * | 10/2008 | Park et al. | 514/473 |

* cited by examiner

*Primary Examiner* — Gina C Justice

(57) ABSTRACT

The present invention relates to preservation of cosmetic formulations. More specifically, the present invention relates to a preservative composition for cosmetic formulations comprising thymol, monolaurin and magnolol obtained from supercritical fluid extracts of *Magnolia officinalis*.

2 Claims, No Drawings

PRESERVATIVE SYSTEM FOR COSMETIC FORMULATIONS—COMPOSITIONS AND METHODS THEREOF

The present application is a divisional application of U.S. Non-provisional application Ser. No. 12/434,747 filed on May 4, 2009, now abandoned.

FIELD OF THE INVENTION

The invention in general relates to methods of preserving cosmetic/personal care formulations to enhance shelf life and stability. In particular, the present invention discloses a novel method of preserving cosmetic/personal care formulations through a two component preservative system, said system comprising (a) Component I which functions to get rid of the existing microbial load (contamination) in a natural cosmetic formulation base using an optimized pasteurization method that does not involve the step of deep freezing; and (b) Component II that includes the step of adding synergistic blends of fractionated essential oils, extracts and isolated compounds to the pre-pasteurized cosmetic base obtained through the method of component I, wherein the said synergistic blends sustain the effects of pasteurization through anti-microbial and anti-oxidant effects, said anti-oxidant effects further enhancing anti-microbial effects by virtue of inhibiting lipid per oxidation that facilitates the undue proliferation of microbes.

DESCRIPTION OF PRIOR ART

A preservation system helps maintain the integrity of a finished cosmetic/personal care formulations. Preservation of cosmetic formulations has largely been addressed as control mechanisms for bacterial adaptation and contamination in such formulations. Prior art include, I. Cosmetic Microbiology—A Practical Handbook by Daniel K. Brannan CRC PRESS;
 II. Modern Cosmeticology: The Principles and Practice of Modern Cosmetics by Ralph Gordon Harry;
 III. Disinfection, Sterilization, and Preservation by Seymour Stanton Block, Carl Adam Lawrence;
 IV. Cosmetic Microbiology: A Practical Approach by Phil Geis, Philip A. Geis]

U.S. Pat. No. 4,416,901 titled "Process for prolonging the shelf life of cosmetics" on Nov. 22, 1983 discusses a process for prolonging the shelf-life and the period of resistance to microorganisms of cosmetics comprising (a) Subjecting said cosmetic comprising an oil-in-water emulsion to pasteurization while under vacuum or inert gas atmosphere by heating to a temperature of from about 60° C. to about 75° C.
(b) Deep freezing said pasteurized cosmetic to a temperature of below about −100° C. and
(c) Maintaining the pasteurized cosmetic for about 45 days at about −20° C. to about −40°C.

This patent addresses pasteurization alone as a method to prolong the shelf life of the cosmetic. Some of the innate constraints possible with pasteurization are (i) the process is prolonged. It requires long periods of storing the pasteurized cosmetic at freezing temperatures; (ii) Pasteurization is not a sterilization method. It only ensures disinfection to the maximal level. Handling pasteurized products requires extreme care; (iii) Maintenance of the pasteurization effect is also very difficult. Hence pasteurization alone may not be enough to prolong the shelf life of cosmetic formulations.

The natural preservative (anti-microbial) effect of heated garlic is discussed in United States Patent Application 20050031715.

A natural preservative from the seeds of *Citrus paradisi* having excellent safety, excellent as bactericidal, antibiotic and sterilizing activity for meat preservation is discussed in JP02303446.

U.S. Pat. No. 7,214,392 discusses a natural preservative composition for inhibiting the growth of microorganisms in food products.

U.S. Pat. No. 7,429,396 discusses natural anti-fungal (anti-dermatophytic) preservative compositions for use in cosmetics.

The auto-oxidation of hydrocarbons, in particular unsaturated hydrocarbons in cosmetics as a result of exposure to air occurs as distinct stages of lipid per oxidation. Stages include, I. Initiation where oxygen free radicals attach lipid molecules to form lipid radicals. The formation of oxygen free radicals is induced by metal ions, enzymes, heat, exposure to sunlight, degree of unsaturation, and pigments.
 II. Propagation where lipid radicals react with oxygen to form peroxides which further react with other fatty acids to form hydro peroxides and other lipid radicals.
 III. Termination where peroxides form stable products while hydro peroxides decompose into aldehydes, ketones, alcohols and acids that contribute to the rancidity and degradation of the cosmetic product.

The publication titled "Are the increases in local tumor necrosis factor and lipid peroxidation observed in pre-starved mice infected with *Salmonella typhimurium* markers of increased liver damage?" Microbes and Infection; Volume 8, Issue 7, June 2006, Pages 1695-1701 indicates that pathogenic microbes are sensitive to cellular stress signals, including oxidative stress. Lipid peroxidation at the cellular level has been shown to act as a signal that enhances multiplication and spread of pathogenic microbes.

Thus, a good preservative function carries a wider perspective in including both efficacious antimicrobial and antioxidant effects. The preservatives used widely in Cosmetic industry include parabens, imidazolidinyl urea, DMDM Hydantoin, Quaternium −15, phenoxyethanol and formaldehyde. However environmental concerns prevail regarding the usage of such chemical preservatives. For example, the potential hazards of paraben usage are cited in the underlying prior art.

(i) Parabens as a risk to the aquatic fauna. (*Environmental Health Perspective Vol* 107(6):2003)
(ii) Scientists in Europe identified Parabens as a potential endocrine disrupting chemicals in the bodies of fishes, human breast milk (*An overview of Endocrine disruptor: Project financed by European Commission under 4th & 5th Framework program.* 2003)
(iii) Parabens can cause skin irritation and contact dermatitis in individuals with Paraben allergies. (Nagel J E et al. *JAMA* 237(5) 1594-5:1977)
(iv) The penetration of Parabens into skin is influenced by its lipophilicity—which provokes accumulation of these molecules into skin; potential cause of skin toxicities. (Rastogi et al; *Experimental Dermatology:* 16(10): 830-836:2007)

With chemical preservatives under scrutiny by regulatory/scientific bodies and increased anti-microbial resistance to such compounds there is an impetus to develop botanical alternatives to chemical preservatives. However, the natural plant based preservatives as discussed in US20050031715, JP02303446, U.S. Pat. Nos. 7,214,392 and 7,429,396 all address preservation in a narrow perspective by addressing only the anti-microbial effects without explaining how their inventions would address the twin component of preservation namely anti-oxidant effects.

It would be more appropriate to develop preservative systems where natural preservative compositions include ingredients that have both anti-microbial and anti-oxidant effects, wherein the said anti-oxidant effects of the ingredients may synergistically enhance the anti-microbial efficacy by inhibiting the deleterious effects of lipid peroxidation as discussed herein above.

The present inventors have hence sought to develop a natural plant material based preservative system for cosmetics that dually functions as a sustained anti-microbial and anti-oxidant system and thus would enhance the shelf life of such cosmetic and personal care formulations.

Accordingly, it is the principle object of the present invention to disclose a novel method of preserving cosmetic/personal care formulations through a two component preservative system, said system comprising (a) Component I which functions to get rid of the existing microbial load (contamination) in a natural cosmetic formulation base using an optimized pasteurization method that does not involve the step of deep freezing; and (b) Component II that includes the step of adding synergistic blends of fractionated essential oils, extracts and isolated compounds to the pre-pasteurized cosmetic base obtained through the method of component I, wherein the said synergistic blends sustain the effects of pasteurization through anti-microbial and anti-oxidant effects, said anti-oxidant effects further enhancing anti-microbial effects by virtue of inhibiting lipid per oxidation that facilitates the undue proliferation of microbes.

It is another objective of the present invention to disclose a two component preservative system, said system comprising (a) Component I which functions to get rid of the existing microbial load (contamination) in a natural cosmetic formulation base using an optimized pasteurization method that does not involve the step of deep freezing; and (b) Component II that includes the step of adding synergistic blends of fractionated essential oils, extracts and isolated compounds to the pre-pasteurized cosmetic base obtained through the method of component I, wherein the said synergistic blends sustain the effects of pasteurization through anti-microbial and anti-oxidant effects, said anti-oxidant effects further enhancing anti-microbial effects by virtue of inhibiting lipid per oxidation that facilitates the undue proliferation of microbes.

It is yet another objective to disclose optimally preserved cosmetic compositions, said compositions preserved by a two-component system, said system comprising (a) Component I which functions to get rid of the existing microbial load (contamination) in a natural cosmetic formulation base using an optimized pasteurization method that does not involve the step of deep freezing; and Component II that includes the step of adding synergistic blends of fractionated essential oils, extracts and isolated compounds to the pre-pasteurized cosmetic base obtained through the method of component I, wherein the said synergistic blends sustain the effects of pasteurization through anti-microbial and anti-oxidant effects, said anti-oxidant effects further enhancing anti-microbial effects by virtue of inhibiting lipid peroxidation that facilitates the undue proliferation of microbes.

Still further, it is an objective of the present invention to disclose natural preservative compositions including synergistic blends of essential oil fractions and extracts selected from the group consisting of Cinnamaldehyde (90-95%); Thymol (95-98%), Eugenol (95-99%), Citral (85-90%), Monolaurin (Assay –90%), Garcinol (Assay –97%), and supercritical fluid extracts of *Magnolia officinalis* comprising Magnolol and honokiol, with a dual mode of action including anti-microbial and anti-oxidant effects wherein said anti-oxidant effects synergistically enhance anti-microbial preservative effect by inhibiting lipid peroxidation that facilitates undue proliferation of microbes.

The present invention meets the aforesaid objectives and provides further related advantages.

SUMMARY OF THE INVENTION

The present invention discloses a novel method of preserving cosmetic/personal care formulations through a two component preservative system, said system comprising (a) Component I which functions to get rid of the existing microbial load (contamination) in a natural cosmetic formulation base using an optimized pasteurization method that does not involve the step of deep freezing; and (b) Component II that includes the step of adding synergistic blends of fractionated essential oils, extracts and isolated compounds to the pre-pasteurized cosmetic base obtained through the method of component I, wherein the said synergistic blends sustain the effects of pasteurization through anti-microbial and anti-oxidant effects, said anti-oxidant effects further synergistically enhancing the anti-microbial preservative effects by virtue of inhibiting lipid per oxidation that facilitates the undue proliferation of microbes. Also disclosed are A. Optimally preserved cosmetic compositions, said compositions preserved by a two-component system, said system comprising (a) Component I which functions to get rid of the existing microbial load (contamination) in a natural cosmetic formulation base using an optimized pasteurization method that does not involve the step of deep freezing; and Component II that includes the step of adding synergistic blends of fractionated essential oils, extracts and isolated compounds to the pre-pasteurized cosmetic base obtained through the method of component I, wherein the said synergistic blends sustain the effects of pasteurization through anti-microbial and anti-oxidant effects, said anti-oxidant effects further enhancing anti-microbial effects by virtue of inhibiting lipid peroxidation that facilitates the undue proliferation of microbes.

B. Natural preservative compositions including synergistic blends of essential oil fractions and extracts selected from the group consisting of Cinnamaldehyde (90-95%); Thymol (95-98%), Eugenol (95-99%), Citral (85-90%), Monolaurin (Assay –90%), Garcinol (Assay –97%), and supercritical fluid extracts of *Magnolia officinalis* comprising (a) magnolol and (b) honokiol, with a dual mode of action including anti-microbial and anti-oxidant effects wherein said anti-oxidant effects synergistically enhance anti-microbial preservative effect by inhibiting lipid peroxidation that facilitates undue proliferation of microbes.

The aforesaid inventive concepts of the present invention also summarize its advantageous features over available prior art.

DESCRIPTION OF THE MOST PREFERRED EMBODIMENT

In the most preferred embodiment the present invention discloses a method of preserving cosmetic formulations through a two-component preservative system wherein component I (an optimized pasteurization method without the deep-freezing step) would serve to reduce the microbial load (logarithmic reduction) of the cosmetic base to bare minimal levels and component II (synergistic blends of fractionated essential oils, extracts and isolated compounds) that would provide sustained anti-microbial and anti-oxidant effects to the previously pasteurized cosmetic base to ensure the safety, freshness and quality of the cosmetic formulation. More preferably, the optimized pasteurization method for reducing the microbial load of cosmetic base to bare minimal levels (component I) comprise the steps of:

1. Dispensing 10 g of the natural cream base comprising naturally occurring microbial contamination into a sterile test tube.
2. Assessing the pre-pasteurization microbial load.
3. Placing the contaminated cosmetic base in a water bath at 63° C. for 30 minutes.
4. Removing the cosmetic base from the water bath and allow to gradually cool to room temperature. This step is unique to the application of pasteurization to cosmetic formulations. The step is in contrast to the phenomenon of deep-freezing followed in conventional pasteurization methods. Deep freezing may not be suitable for cosmetic bases due to the underlying innate disadvantages.
   a) The gradual degradation of desirable physical properties of cosmetic base including texture, stability and viscosity.
   b) Undesirable changes in the cosmetic base due to the changes that deep-freezing may cause on proteins and fats. Fats in particular may be subjected to the process of auto-oxidation or hydrolysis to yield molecules that may react adversely with proteins or free amino acids to alter the physical characteristics of the cosmetic base.

Gradual cooling at room temperature has been shown by the inventors to considerably reduce the microbial load without affecting desirable physical properties of the cosmetic base.

5. Analyzing the post-pasteurization microbial load.

Further, component II comprises the steps of adding synergistic blends of essential oils or fractions thereof and extracts that possess both anti-oxidant and anti-microbial properties. More specifically, the synergistic blends of essential oil fractions are selected from the group consisting of Cinnamaldehyde (90-95%); Thymol (95-98%), Eugenol (95-99%), Citral (85-90%), Monolaurin (Assay ~90%), Garcinol (Assay ~97%), and supercritical fluid extracts of *Magnolia officinalis* comprising (a) Magnolol and (b) Honokiol.

Still more specifically, the synergistic blends of fractionated essential oils, extracts and isolated compounds include A. About 22% w/w of the blend cinnamaldehyde (assay 90-95%), from about 14%-15% w/w of the blend Thymol (Assay 95%-98%), about 15% w/w of the blend Eugenol (Assay 95% to 99%), about 17% to about 18% w/w of the blend Citral (Assay 85% to 90%), about 28% to 29% of monolaurin and about 3% w/w of the blend garcinol (Assay 97%).

B. About 17% to about 18% w/w of the blend cinnamaldehyde (assay 90-95%), from about 11% to about 12% w/w of the blend Thymol (Assay 95%-98%), about 12% w/w of the blend Eugenol (Assay 95% to 99%), about 14% w/w of the blend Citral (Assay 85% to 90%) and about 45% Monolaurin (Assay ~90%).

C. About 61% w/w of the blend Thymol (Assay 95%-98%), about 38% w/w of the blend Monolaurin (Assay ~90%) and 1% w/w of isolated magnolol obtained from the supercritical fluid extracts of *Magnolia officinalis* comprising Magnolol and honokiol.

D. About 19% w/w of the blend Thymol (Assay 95%-98%), about 20% to about 22% w/w of the blend Eugenol (assay 95% to 99%), about 23% to 24% w/w of the blend Citral (Assay 85% to 90%) and about 37% to 38% Monolaurin (Assay 90%).

With lipid per oxidation being implicated as an important cause of cosmetic degradation and the popular hypothesis that not all efficacious anti-microbials may be good anti-oxidant substances, the present inventors have surprisingly detected excellent anti-oxidant potential of fractionated anti-microbial essential oils, the said anti-oxidant potential exponentially enhancing (synergy) the anti-microbial preservative effects through antioxidant mechanisms.

In another preferred embodiment, the present invention includes optimally preserved cosmetic compositions, said compositions preserved by a two-component system, said system comprising (a) Component I which functions to get rid of the existing microbial load (contamination) in a natural cosmetic formulation base using an optimized pasteurization method that does not involve the step of deep freezing; and Component II that includes the step of adding synergistic blends of fractionated essential oils, extracts and isolated compounds to the pre-pasteurized cosmetic base obtained through the method of component I, wherein the said synergistic blends sustain the effects of pasteurization through anti-microbial and anti-oxidant effects, said anti-oxidant effects further enhancing anti-microbial effects by virtue of inhibiting lipid peroxidation that facilitates the undue proliferation of microbes. More specifically, the synergistic blends of essential oil fractions and extracts are selected from the group consisting of Cinnamaldehyde (90-95%); Thymol (95-98%), Eugenol (95-99%), Citral (85-90%), Monolaurin (Assay ~90%), Garcinol (Assay ~97%), and supercritical fluid extracts of *Magnolia officinalis* comprising Magnolol and honoldol.

Still more specifically, the synergistic blends of fractionated essential oils, extracts and isolated compounds include A. About 22% w/w of the blend cinnamaldehyde (assay 90-95%), from about 14%-15% w/w of the blend Thymol (Assay 95%-98%), about 15% w/w of the blend Eugenol (Assay 95% to 99%), about 17% to about 18% w/w of the blend Citral (Assay 85% to 90%), about 28% to 29% of monolaurin and about 3% w/w of the blend garcinol (Assay 97%).

B. About 17% to about 18% w/w of the blend cinnamaldehyde (assay 90-95%), from about 11% to about 12% w/w of the blend Thymol (Assay 95%-98%), about 12% w/w of the blend Eugenol (Assay 95% to 99%), about 14% w/w of the blend Citral (Assay 85% to 90%) and about 45% Monolaurin (Assay ~90%).

C. About 61% w/w of the blend Thymol (Assay 95%-98%), about 38% w/w of the blend Monolaurin (Assay ~90%) and 1% w/w of isolated magnolol obtained from the supercritical fluid extracts of *Magnolia officinalis* comprising Magnolol and honokiol.

D. About 19% w/w of the blend Thymol (Assay 95%-98%), about 20% to about 22% w/w of the blend Eugenol (assay 95% to 99%), about 23% to 24% w/w of the blend Citral (Assay 85% to 90%) and about 37% to 38% Monolaurin (Assay 90%)

In yet another preferred embodiment, the present invention includes natural preservative compositions including synergistic blends of essential oil fractions and extracts selected from the group consisting of Cinnamaldehyde (90-95%); Thymol (95-98%), Eugenol (95-99%), Citral (85-90%), Monolaurin (Assay ~90%), Garcinol (Assay ~97%), and supercritical fluid extracts of *Magnolia officinalis* comprising Magnolol and honokiol, with a dual mode of action including anti-microbial and anti-oxidant effects wherein said anti-oxidant effects synergistically enhance anti-microbial preservative effect by inhibiting lipid peroxidation that facilitates undue proliferation of microbes. More specifically, the synergistic blends of essential oil fractions and extracts are selected from the group consisting of Cinnamaldehyde (90-95%); Thymol (95-98%), Eugenol (95-99%), Citral (85-90%), Monolaurin (Assay –90%), Garcinol (Assay –97%), and supercritical fluid extracts of *Magnolia officinalis* comprising Magnolol and Honokiol.

Still more specifically, the synergistic blends of fractionated essential oils, extracts and isolated compounds include A. About 22% w/w of the blend cinnamaldehyde (assay 90-95%), from about 14%-15% w/w of the blend Thymol (Assay 95%-98%), about 15% w/w of the blend Eugenol (Assay 95% to 99%), about 17% to about 18% w/w of the blend Citral (Assay 85% to 90%), about 28% to 29% of monolaurin and about 3% w/w of the blend garcinol (Assay 97%).

B. About 17% to about 18% w/w of the blend cinnamaldehyde (assay 90-95%), from about 11% to about 12% w/w of the blend Thymol (Assay 95%-98%), about 12% w/w of the blend Eugenol (Assay 95% to 99%), about 14% w/w of the blend Citral (Assay 85% to 90%) and about 45% Monolaurin (Assay –90%).

C. About 61% w/w of the blend Thymol (Assay 95%-98%), about 38% w/w of the blend Monolaurin (Assay –90%) and about 1% w/w of isolated magnolol obtained from the supercritical fluid extracts of *Magnolia officinalis* comprising Magnolol and honokiol.

D. About 19% w/w of the blend Thymol (Assay 95%-98%), about 20% to about 22% w/w of the blend Eugenol (assay 95% to 99%), about 23% to 24% w/w of the blend Citral (Assay 85% to 90%) and about 37% to 38% Monolaurin (Assay 90%).

In an alternate embodiment, the present invention also includes Antioxidant compositions, said compositions including synergistic blends of essential oil fractions, extracts and isolated compounds selected from the group consisting of Cinnamaldehyde (90-95%); Thymol (95-98%), Eugenol (95-99%), Citral (85-90%), Monolaurin (Assay –90%), Garcinol (Assay –97%), and supercritical fluid extracts of *Magnolia officinalis* comprising Magnolol and Honokiol.

Still more specifically, the synergistic blends of fractionated essential oils, extracts and isolated compounds include A. About 22% w/w of the blend cinnamaldehyde (assay 90-95%), from about 14%-15% w/w of the blend Thymol (Assay 95%-98%), about 15% w/w of the blend Eugenol (Assay 95% to 99%), about 17% to about 18% w/w of the blend Citral (Assay 85% to 90%), about 28% to 29% of monolaurin and about 3% w/w of the blend garcinol (Assay 97%).

B. About 17% to about 18% w/w of the blend cinnamaldehyde (assay 90-95%), from about 11% to about 12% w/w of the blend Thymol (Assay 95%-98%), about 12% w/w of the blend Eugenol (Assay 95% to 99%), about 14% w/w of the blend Citral (Assay 85% to 90%) and about 45% Monolaurin (Assay –90%).

C. About 61% w/w of the blend Thymol (Assay 95%-98%), about 38% w/w of the blend Monolaurin (Assay –90%) and 1% w/w of isolated magnolol obtained from the supercritical fluid extracts of *Magnolia officinalis* comprising Magnolol and honokiol.

D. About 19% w/w of the blend Thymol (Assay 95%-98%), about 20% to about 22% w/w of the blend Eugenol (assay 95% to 99%), about 23% to 24% w/w of the blend Citral (Assay 85% to 90%) and about 37% to 38% Monolaurin (Assay 90%).

In another alternate embodiment, the present invention also includes antimicrobial compositions, said compositions including synergistic blends of essential oil fractions, extracts and isolated compounds selected from the group consisting of Cinnamaldehyde (90-95%); Thymol (95-98%), Eugenol (95-99%), Citral (85-90%), Monolaurin (Assay –90%), Garcinol (Assay –97%), and supercritical fluid extracts of *Magnolia officinalis* comprising Magnolol and Honokiol.

Still more specifically, the synergistic blends of fractionated essential oils, extracts and isolated compounds include A. About 22% w/w of the blend cinnamaldehyde (assay 90-95%), from about 14%-15% w/w of the blend Thymol (Assay 95%-98%), about 15% w/w of the blend Eugenol (Assay 95% to 99%), about 17% to about 18% w/w of the blend Citral (Assay 85% to 90%), about 28% to 29% of monolaurin and about 3% w/w of the blend garcinol (Assay 97%).

B. About 17% to about 18% w/w of the blend cinnamaldehyde (assay 90-95%), from about 11% to about 12% w/w of the blend Thymol (Assay 95%-98%), about 12% w/w of the blend Eugenol (Assay 95% to 99%), about 14% w/w of the blend Citral (Assay 85% to 90%) and about 45% Monolaurin (Assay –90%).

C. About 61% w/w of the blend Thymol (Assay 95%-98%), about 38% w/w of the blend Monolaurin (Assay –90%) and 1% w/w of isolated magnolol obtained from the supercritical fluid extracts of *Magnolia officinalis* comprising Magnolol and honokiol.

D. About 19% w/w of the blend Thymol (Assay 95%-98%), about 20% to about 22% w/w of the blend Eugenol (assay 95% to 99%), about 23% to 24% w/w of the blend Citral (Assay 85% to 90%) and about 37% to 38% Monolaurin (Assay 90%).

More specifically the microbes mentioned in the aforesaid paragraphs include bacteria and fungi.

Still more specifically, the bacteria include both Gram positive and Gram negative organisms. Further, the bacteria include both cocci and bacilli. Specifically the bacteria may be one selected from the group consisting of *Staphylococcus aureus, Escherichia coli* and *Pseudomonas aeruginosa*.

Still more specifically, the fungi may be one belonging to the Zygomycetes, Ascomycetes, Basidiomycetes or Fungi imperfecti. Further, the fungi may include yeast or mold forms. In specific the fungi are *Candida albicans* and *Aspergillus niger*.

The results of such anti-microbial and anti-oxidant effects of fractionated essential oils, extracts and isolated compounds are presented herein below as specific examples for reference.

EXAMPLE I

Anti-Microbial Efficacy of Fractionated Essential Oil Blends

Percentage compositions of the blends I, II, III and IV

TABLE A

| | | Blend I | |
|---|---|---|---|
| S. No. | Plant material | Active Essential Oil fractions/Extracts | % composition (w/w of the blend) |
| 1. | Cinnamon | 90-95% Cinnamaldehyde | 21.88 |
| 2 | Thyme | 95-98% Thymol | 14.36 |
| 3. | Clove | 95-99% Eugenol | 15.26 |
| 4. | Lemon grass | 85-90% Citral | 17.62 |
| 5. | Monolaurin | Monolaurin (Assay—90%) | 28.05 |
| 6. | Garcinol | Garcinol (Assay—97%) | 2.80 |

TABLE B

Blend II

| S. No. | Plant material | Active Essential Oil fractions/Extract | % composition (w/w of the blend) |
|---|---|---|---|
| 1. | Cinnamon | 90-95% Cinnamaldehyde | 17.47 |
| 2 | Thyme | 95-98% Thymol | 11.47 |
| 3. | Clove | 95-99% Eugenol | 12.18 |
| 4. | Lemon grass | 85-90% Citral | 14.067 |
| 5. | Monolaurin | Monolaurin (Assay—90%) | 44.80 |

TABLE C

Blend III

| S. No. | Constituent | Active Essential Oil fractions/Extracts | % composition (w/w of the blend) |
|---|---|---|---|
| 1. | Thyme | Thymol (Assay 95—98%) | 61.04 |
| 2. | Monolaurin | Monolaurin (Assay—90%) | 38.00 |
| 3. | SCFE extracts from *Magnolia officinalis* containing magnolol and honokiol | Isolated Magnolol | 0.95 |

TABLE D

Blend IV

| S. No. | Constituent | Active Essential Oil fractions/Extracts | % composition (w/w of the blend) |
|---|---|---|---|
| 1. | Thyme | 95-98% Thymol | 19% |
| 2. | Clove | 95-99% Eugenol | 21% |
| 3. | Lemon grass | 85-90% Citral | 23% |
| 4. | Monolaurin | Monolaurin (Assay—90%) | 37% |

TABLE E

ANTI-MICROBIAL ACTIVITY OF NATURAL PRESERVATIVE BLENDS IN TERMS OF MINIMUM INHIBITORY CONCENTRATION

| | MIC concentration (%) of Preservative Blends | | | |
|---|---|---|---|---|
| Target Organisms | BLEND I | BLEND II | BLEND III | BLEND IV |
| S. aureus | 0.07 | 0.07 | 0.075 | 0.07 |
| E. coli | 0.07 | 0.07 | 0.4 | 0.07 |
| C. albicans | 0.07 | 0.07 | 0.075 | 0.07 |

TABLE F

ANTI-OXIDANT POTENTIAL OF FRACTIONATED ESSENTIAL OIL and EXTRACT BLENDS

| BLENDS | ORAC VALUES | DPPH ($IC_{50}$) |
|---|---|---|
| I | 4349.75 ± 1202 μmol TE/g | 9.394 μg/ml |
| II | 3729 ± 1076 μmol TE/g | 14.04 μg/ml |
| III | 6964 ± 990 μmol TE/g | 57.31 μg/ml |
| IV | 5006 ± 783 μmol TE/g | 8.149 μg/ml |

Natural preservative blends I, II, III and IV thus show excellent anti-microbial effects which are due to (i) direct effects of the ingredients included in the blend on pathogenic microbes as evinced by the MIC and (ii) indirect effects of the ingredients included in the blend on microbial growth, through the inhibition of lipid per oxidation as evinced by ORAC and DPPH scavenging activities. It thus becomes evident, that such blends when incorporated to a pre-pasteurized cosmetic base would help preserve the effects of pasteurization by virtue of synergistically acting anti-oxidant and anti-microbial effects, wherein the anti-oxidant effects further enhance anti-microbial effects by inhibiting lipid per oxidation that facilitates the undue proliferation of microbes.

Evaluation of Microbial Load of Challenged and Pasteurized Cosmetic Bases

The plain cream base was challenged with microbial cultures; the counts were determined and then pasteurized. The selected natural preservatives were incorporated in the pasteurized cream base and tested for microbial load at intervals of 7 days, 14 days, 21 days, 28 days, 2 months and 3 months.

TABLE G

Organism: *Staphylococcus aureus* ATCC6538
Initial Count: $9 \times 10^6$ cfu/ml

| | Preservative added to the pasteurized base | Test intervals | | | | | | |
|---|---|---|---|---|---|---|---|---|
| | | 0 days | 7 days | 14 days | 21 days | 28 days | 2 months | 3 months |
| Plain Base Pasteurized by the method of the instant invention | Blend I (0.5%) | <10 | 10 | <10 | <10 | <10 | <10 | <10 |
| | Blend I (1.0%) | <10 | <10 | <10 | <10 | <10 | <10 | <10 |
| | Blend I (1.5%) | <10 | <10 | <10 | <10 | <10 | <10 | <10 |
| | Blend II (0.5%) | <10 | <10 | <10 | <10 | <10 | <10 | <10 |
| | Blend II (1.0%) | <10 | <10 | <10 | <10 | <10 | <10 | <10 |
| | Blend II (1.5%) | <10 | <10 | <10 | <10 | <10 | <10 | <10 |
| | Blend III (0.5%) | <10 | <10 | <10 | <10 | <10 | <10 | <10 |
| | Blend III (1.0%) | <10 | <10 | <10 | <10 | <10 | <10 | <10 |
| | Blend III (1.5%) | <10 | <10 | <10 | <10 | <10 | <10 | <10 |
| | Blend IV (0.5%) | <10 | <10 | <10 | <10 | <10 | <10 | <10 |
| | Blend IV (1.0%) | <10 | <10 | <10 | <10 | <10 | <10 | <10 |
| | Blend IV (1.5%) | <10 | <10 | <10 | <10 | <10 | <10 | <10 |

TABLE H

Organism: *E. coli* ATCC8739
Initial Count: $38 \times 10^6$ cfu/ml

| | Preservative added to the pasteurized base | \multicolumn{7}{c}{Test intervals} | | | | | | |
|---|---|---|---|---|---|---|---|---|
| | | 0 days | 7 days | 14 days | 21 days | 28 days | 2 months | 3 months |
| Plain Base | Blend I (0.5%) | <10 | <10 | <10 | <10 | <10 | <10 | <10 |
| Pasteurized | Blend I (1.0%) | <10 | <10 | <10 | <10 | <10 | <10 | <10 |
| by the method | Blend I (1.5%) | <10 | <10 | <10 | <10 | <10 | <10 | <10 |
| of the instant | Blend II (0.5%) | <10 | <10 | <10 | <10 | <10 | <10 | <10 |
| invention | Blend II (1.0%) | <10 | <10 | <10 | <10 | <10 | <10 | <10 |
| | Blend II (1.5%) | <10 | <10 | <10 | <10 | <10 | <10 | <10 |
| | Blend III (0.5%) | <10 | <10 | <10 | <10 | <10 | <10 | <10 |
| | Blend III (1.0%) | <10 | <10 | <10 | <10 | <10 | <10 | <10 |
| | Blend III (1.5%) | <10 | <10 | <10 | <10 | <10 | <10 | <10 |
| | Blend IV (0.5%) | <10 | <10 | <10 | <10 | <10 | <10 | <10 |
| | Blend IV (1.0%) | <10 | <10 | <10 | <10 | <10 | <10 | <10 |
| | Blend IV (1.5%) | <10 | <10 | <10 | <10 | <10 | <10 | <10 |

TABLE K

Organism: *Candida albicans* NCIM3471
Initial Count: $4.6 \times 10^6$ cfu/ml

| | Preservative added to the pasteurized base | \multicolumn{7}{c}{Test intervals} | | | | | | |
|---|---|---|---|---|---|---|---|---|
| | | 0 days | 7 days | 14 days | 21 days | 28 days | 2 months | 3 months |
| Plain Base | Blend I (0.5%) | 20 | <10 | <10 | <10 | <10 | <10 | <10 |
| Pasteurized by | Blend I (1.0%) | 30 | <10 | <10 | <10 | <10 | <10 | <10 |
| the method of | Blend I (1.5%) | 30 | <10 | <10 | <10 | <10 | <10 | <10 |
| the instant | Blend II (0.5%) | 20 | <10 | <10 | <10 | <10 | <10 | <10 |
| invention | Blend II (1.0%) | 20 | <10 | <10 | <10 | <10 | <10 | <10 |
| | Blend II (1.5%) | 20 | <10 | <10 | <10 | <10 | <10 | <10 |
| | Blend III (0.5%) | <10 | <10 | <10 | <10 | <10 | <10 | <10 |
| | Blend III (1.0%) | <10 | <10 | <10 | <10 | <10 | <10 | <10 |
| | Blend III (1.5%) | <10 | <10 | <10 | <10 | <10 | <10 | <10 |
| | Blend IV (0.5%) | <10 | <10 | <10 | <10 | <10 | <10 | <10 |
| | Blend IV (1.0%) | <10 | <10 | <10 | <10 | <10 | <10 | <10 |
| | Blend IV (1.5%) | <10 | <10 | <10 | <10 | <10 | <10 | <10 |

TABLE L

Organism: *Pseudomonas aeruginosa* NCIM2200
Initial Count: $26 \times 10^6$ cfu/ml

| | Preservative added to the pasteurized base | \multicolumn{7}{c}{Test intervals} | | | | | | |
|---|---|---|---|---|---|---|---|---|
| | | 0 days | 7 days | 14 days | 21 days | 28 days | 2 months | 3 months |
| Plain Base | Blend I (0.5%) | <10 | <10 | <10 | <10 | <10 | <10 | <10 |
| Pasteurized by | Blend I (1.0%) | <10 | <10 | <10 | <10 | <10 | <10 | <10 |
| the method of | Blend I (1.5%) | <10 | <10 | <10 | <10 | <10 | <10 | <10 |
| the instant | Blend II (0.5%) | <10 | <10 | <10 | <10 | <10 | <10 | <10 |
| invention | Blend II (1.0%) | <10 | <10 | <10 | <10 | <10 | <10 | <10 |
| | Blend II (1.5%) | <10 | <10 | <10 | <10 | <10 | <10 | <10 |
| | Blend III (0.5%) | <10 | <10 | <10 | <10 | <10 | <10 | <10 |
| | Blend III (1.0%) | <10 | <10 | <10 | <10 | <10 | <10 | <10 |
| | Blend III (1.5%) | <10 | <10 | <10 | <10 | <10 | <10 | <10 |
| | Blend IV (0.5%) | <10 | <10 | <10 | <10 | <10 | <10 | <10 |
| | Blend IV (1.0%) | <10 | <10 | <10 | <10 | <10 | <10 | <10 |
| | Blend IV (1.5%) | <10 | <10 | <10 | <10 | <10 | <10 | <10 |

TABLE M

Organism: *Aspergillus niger* NCIM1196
Initial Count: 7 × 10⁵ cfu/ml

|  | Preservative added to the pasteurized base | Test intervals |  |  |  |  |  |  |
|---|---|---|---|---|---|---|---|---|
|  |  | 0 days | 7 days | 14 days | 21 days | 28 days | 2 months | 3 months |
| Plain Base | Blend I (0.5%) | <10 | <10 | <10 | <10 | <10 | <10 | <10 |
| Pasteurized by | Blend I (1.0%) | <10 | <10 | <10 | <10 | <10 | <10 | <10 |
| the method of | Blend I (1.5%) | <10 | <10 | <10 | <10 | <10 | <10 | <10 |
| the instant | Blend II (0.5%) | <10 | <10 | <10 | <10 | <10 | <10 | <10 |
| invention | Blend II (1.0%) | <10 | <10 | <10 | <10 | <10 | <10 | <10 |
|  | Blend II (1.5%) | <10 | <10 | <10 | <10 | <10 | <10 | <10 |
|  | Blend III (0.5%) | <10 | <10 | <10 | <10 | <10 | <10 | <10 |
|  | Blend III (1.0%) | <10 | <10 | <10 | <10 | <10 | <10 | <10 |
|  | Blend III (1.5%) | <10 | <10 | <10 | <10 | <10 | <10 | <10 |
|  | Blend IV (0.5%) | <10 | <10 | <10 | <10 | <10 | <10 | <10 |
|  | Blend IV (1.0%) | <10 | <10 | <10 | <10 | <10 | <10 | <10 |
|  | Blend IV (1.5%) | <10 | <10 | <10 | <10 | <10 | <10 | <10 |

TABLE N

NORMAL STABILITY STUDIES ON THE PRESERVATIVE BLENDS OF THE PRESENT INVENTION

| Product: Natural Preservative blends I, II, III and IV | Sample Pack: Packed in a 30 ml capacity HDPE container Storage Conditions: 25 +− 2° C., 60 +− 5% RH Quantity: About 30 g per analysis | Tests performed 1. Description 2. Density 3. Peroxide value 4. GC profile | Frequency of testing At the intervals of 3, 6, 9, 12, 18, 24, 36, 48 and 60 months |
|---|---|---|---|

| Period of testing | Description | Density | Peroxide value | GC Profile |
|---|---|---|---|---|
| Preservative blend I | | | | |
| Initial | Pale yellow to yellow colored viscous liquid | 0.988 | 10.56 | Complies |
| 3 month | Pale yellow to yellow colored viscous liquid | 0.994 | 3.48 | Complies |
| Preservative Blend II | | | | |
| Initial | Pale yellow to yellow colored viscous liquid | 0.934 | 0.57 | Complies |
| 3 month | Pale yellow to yellow colored viscous liquid | 0.985 | Nil | Complies |
| Preservative Blend III | | | | |
| Initial | Pale yellow to yellow colored viscous liquid | 0.964 | 10.75 | Complies |
| 3 month | Pale yellow to yellow colored viscous liquid | 0.982 | 4.24 | Complies |
| Preservative Blend IV | | | | |
| Initial | Pale yellow to yellow colored viscous liquid | 0.924 | 4.25 | Complies |
| 3 month | Pale yellow to yellow colored viscous liquid | 0.978 | Nil | Complies |

The result of the stability studies on preservative blends I, II, III and IV indicated no adverse changes. It was also observed that there was a significant decrease in the Peroxide value. It must be noted that an increase in peroxide value indicates that the product is rancid.

While the invention has been described with reference to a preferred embodiment, it is to be clearly understood by those skilled in the art that the invention is not limited thereto. Rather, the scope of the invention is to be interpreted only in conjunction with the appended claims.

We claim:

1. A method of simultaneously sustaining both anti-microbial and anti-oxidant effects in pre-pasteurised cosmetic formulations, said method comprising steps of:
   I. Optimal pasteurization comprising,
      a) Dispensing 10 g of the microbially contaminated natural cream base into a sterile test tube;
      b) Assessing pre-pasteurization microbial load in the cream base;
      c) Placing the contaminated cosmetic base in a water bath at 63° C. for 30 minutes;
      d) Removing the cosmetic base from the water bath and allowing it to gradually cool; and
   II. Adding in effective amounts of a natural preservative composition to the cosmetic base pasteurized by step I, said composition comprising thymol, monolaurin and magnolol obtained from supercritical fluid extracts of *Magnolia officinalis*.

2. The method as claimed in claim 1, wherein the composition comprises from about 61% w/w of thymol, about 38% of monolaurin and about 1% w/w of magnolol obtained from supercritical fluid extracts of *Magnolia officinalis*.

* * * * *